US005626572A

United States Patent [19]
Ahr et al.

[11] Patent Number: 5,626,572
[45] Date of Patent: May 6, 1997

[54] ABSORBENT ARTICLE WITH MULTIPLE FLAPS

[75] Inventors: Nicholas A. Ahr, Cincinnati; Edward J. Milbrada, West Chester, both of Ohio

[73] Assignee: The Procter & Gamble Company, Cincinnati, Ohio

[21] Appl. No.: 337,700

[22] Filed: Nov. 10, 1994

[51] Int. Cl.⁶ .............. A61F 13/15; A61F 13/20
[52] U.S. Cl. ................... 604/385.1; 604/387
[58] Field of Search ............... 604/385.1, 386, 604/387, 389, 390

[56] References Cited

U.S. PATENT DOCUMENTS

| | | |
|---|---|---|
| 4,795,453 | 1/1989 | Wolfe . |
| 4,900,320 | 2/1990 | McCoy ........................... 604/387 |
| 5,281,209 | 1/1994 | Osborn, III et al. ............ 604/385.1 |
| 5,383,869 | 1/1995 | Osborn, III ..................... 604/385.1 |
| 5,391,162 | 2/1995 | Widlund et al. ................ 604/385.1 |

FOREIGN PATENT DOCUMENTS

| | | |
|---|---|---|
| 0299532A2 | 1/1989 | European Pat. Off. . |
| 0467184A1 | 1/1992 | European Pat. Off. . |
| 0511905A1 | 11/1992 | European Pat. Off. . |
| 2161384 | 1/1986 | United Kingdom . |
| 2195541 | 4/1988 | United Kingdom . |

*Primary Examiner*—John G. Weiss
*Assistant Examiner*—David J. Cho
*Attorney, Agent, or Firm*—Edward J. Milbrada; Jeffrey V. Bamber; Steven W. Miller

[57] ABSTRACT

Absorbent articles with a plurality of transversely extending flap pairs are provided. Longitudinally adjacent flap pairs are joined along a transversely oriented line of weakness. Individual flap pairs are deployed from a retracted position to an extended position by tearing along this line of weakness and transversely extending the flap pair.

21 Claims, 3 Drawing Sheets

ABSORBENT ARTICLE WITH MULTIPLE FLAPS

FIELD OF THE INVENTION

The invention disclosed herein relates to disposable absorbent articles, particularly sanitary napkins, and more particularly sanitary napkins with an adjustable undergarment protection system for providing improved protection against soiling.

BACKGROUND OF THE INVENTION

Sanitary napkins and related disposable absorbent articles which provide for the collection of menses and other bodily discharges are well known in the art. It has long been an object of sanitary napkins to readily intercept menses upon discharge from the wearer. Such sanitary napkins typically have a means, such as pressure sensitive adhesive, for affixing the sanitary napkin to the undergarment of a wearer and for maintaining the sanitary napkin in the proper position to intercept the discharged menses.

However, certain difficulties may arise with current absorbent products. For example, the undergarment may not, in fact, move in concert with the body of the wearer. Specifically, the crotch of the undergarment of the wearer may not be in an optimal position relative to the vaginal opening. In addition, as the wearer spreads her legs, walks, sits, etc., the sanitary napkin may not flex and twist with the undergarment—stressing the means for affixing the sanitary napkin to the undergarment of the wearer. In fact, the pressure sensitive adhesive may become detached from the undergarment, further allowing the sanitary napkin to shift from the desired position and registration with resulting loss of protection.

Several attempts in the art have been made to provide a sanitary napkin which may be attached to the undergarment of the wearer and also maintain the constant position with respect to the body of the wearer. For example, U.S. Pat. No. 4,425,130 issued Jan. 10, 1984 to DesMarais discloses a sanitary napkin having decoupled components joined at the transverse edges. U.S. Pat. No. 5,007,906 issued Apr. 16, 1991 to Osborn III, et al. discloses a sanitary napkin with a topsheet and an absorbent core that are decoupled from the backsheet allowing the topsheet and the backsheet to be separated in the Z-direction.

Attempts have also been made to provide sanitary napkins with improved means for protection of a wearer's undergarment. For example U.S. Pat. No. B1 4,589,876 Reexamination Certificate issued Apr. 27, 1993 to Van Tilburg describes a sanitary napkin with flaps that extend laterally from a longitudinal edge of a central absorbent pad. The flaps contain a flexible axis about which the flap can fold on itself. In use, each flap bends on this axis around the crotch portion of a wearer's panty. U.S. Pat. No. 5,037,418 issued to Kons, et al. on Aug. 6, 1991 discloses an absorbent article designed to be attached to the crotch region of an undergarment. An optionally attachable protective sheet is provided which can wrap the crotch region of the undergarment to prevent staining.

Other attempts have been made to provide sanitary napkins that compensate for pad movement due to wearer motion. Examples include U.S. Pat. No. 4,605,405 issued to Lassen on Aug. 12, 1986 which describes a sanitary napkin with a positioning strap attached to the pad on one end of the strap, a means for attaching the strap to the undergarment on the other end of the strap, and a low friction baffle which is said to allow longitudinal sliding of the pad in response to wearer motion. U.S. Pat. No. 4,609,373 issued to Johnson on Sep. 2, 1986 discloses a perineal pad said to limit the range of possible displacement of the pad. The pad has a strip attached to the pad at one end and attachment means at the other end of the strip. The strip is passed through a loop in an undergarment and then attached to the garment facing side of the pad using the attachment means.

In spite of these efforts, however, the search for improved absorbent articles has continued. In particular, the need exists for a unitary disposable absorbent article which has an alternative undergarment protection system which allows a wearer to position the article in an optimal location and attach it to an undergarment in that location so it remains reliably attached there.

It is an object of this invention to provide a sanitary napkin which more readily intercepts menses as it is discharged. Also, it is an object of this invention to provide a sanitary napkin which remains in an optimal location throughout the range of normal movements encountered while the sanitary napkin is worn. Finally, it is an object of this invention to provide a sanitary napkin which allows a wearer to determine what the optimal location is for her particular needs and attach the sanitary napkin in that location.

SUMMARY OF THE INVENTION

The present invention relates to an absorbent article that includes a central absorbent body having longitudinal sides and transverse ends that comprises a liquid pervious topsheet, a liquid impervious backsheet and an absorbent core positioned between the topsheet and backsheet. The absorbent article further comprises a plurality of flap pairs joined to the central absorbent body. Preferably, the flap pairs are attached to the garment facing side of the absorbent article. Longitudinally adjacent flap pairs are also preferably joined along a transverse line of weakness, such as a perforation pattern or the like. Each flap pair preferably comprises a liquid impervious material, and an attachment adhesive disposed on the garment facing side of each flap comprising the pair. The flap pairs may initially be provided in an extended condition and be separable along the line of weakness. Preferably, the flap pairs are provided in a retracted position (e.g., folded) and can be deployed by a user to an extended position.

The relative position of the central absorbent body and the flap pairs when the absorbent article is worn is determined by which flap pair of the plurality the user chooses to deploy. Absorbent articles of the present invention, thus, allow a user to independently position the central absorbent body and the flaps for maximum comfort and protection. That is, a user can place the absorbent article of the present invention in the optimal location for the user's particular needs.

BRIEF DESCRIPTION OF THE DRAWINGS

While the specification concludes with claims particularly pointing out and distinctly claiming the present invention, it is believed the same will be better understood from the following description taken in conjunction with the accompanying drawings wherein like parts are given the same reference numeral, and:

DETAILED DESCRIPTION OF THE INVENTION

As used herein, the term "absorbent article" refers to devices which absorb and contain body exudates, and, more specifically, to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
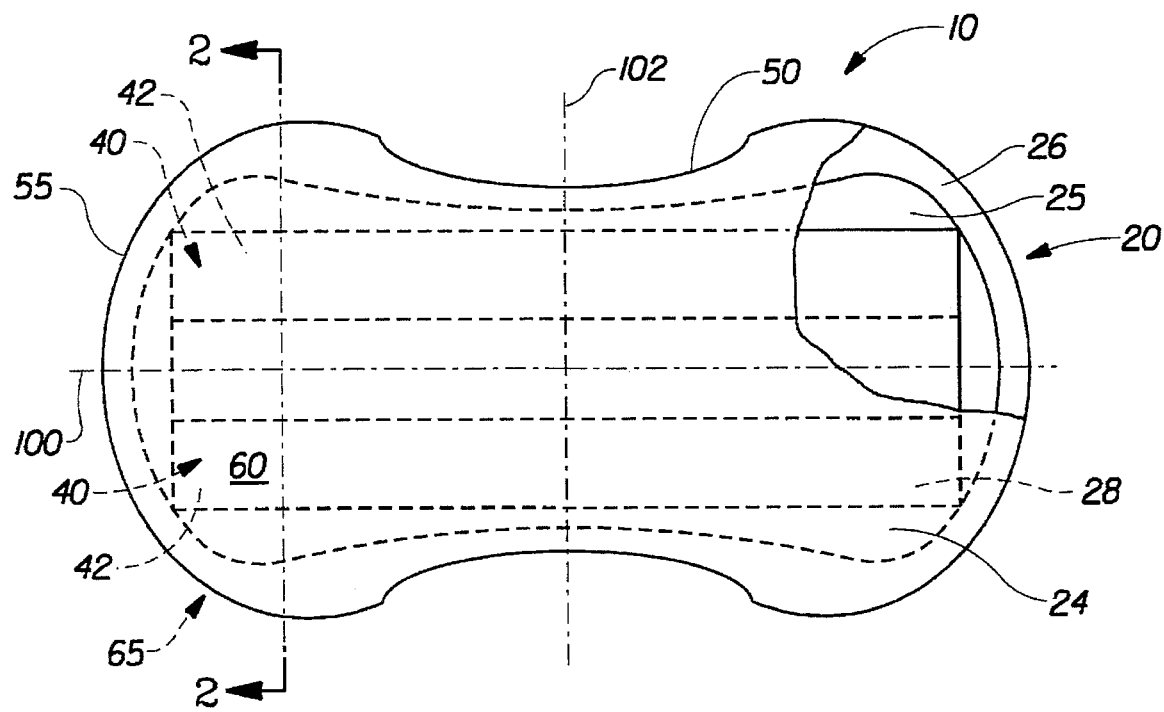
FIG. 1 is a plan view of the body facing side, partially shown in cutaway, of a sanitary napkin according to the present invention.

A preferred embodiment of a unitary disposable absorbent article of the present invention is the catamenial pad, sanitary napkin 10, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, and to other absorbent articles such as incontinence pads, and the like.

FIG. 1 is a plan view of the sanitary napkin 10 of the present invention in its flat-out state with portions of the structure being cut-away to more clearly show the construction of the sanitary napkin 10 and with the portion of the sanitary napkin 10 which faces or contacts the wearer, oriented towards the viewer. The sanitary napkin 10 has two surfaces, a body-contacting surface 60 or "body surface" and a garment surface 65. The sanitary napkin 10 is shown in FIG. 1 as viewed from its body surface. The body surface is intended to be worn adjacent to the body of the wearer while the garment surface is on the opposite side and is intended to be placed adjacent to the wearer's undergarments when the sanitary napkin 10 is worn. As shown in FIG. 1, the sanitary napkin 10 preferably comprises a central absorbent body 20 and an adjustable undergarment protection system 40.

The central absorbent body 20 comprises a liquid pervious topsheet 24, a liquid impervious backsheet 26 joined with the topsheet 24, and an absorbent core 28 positioned between the topsheet 24 and the backsheet 26. FIG. 1 also shows that the central absorbent body 20 has a periphery which is defined by the outer edges of the central absorbent body 20 in which the longitudinal edges are designated 50 and the end edges are designated 55. The central absorbent body 20 further has a longitudinal centerline 100 and a transverse centerline 102. The term "longitudinal", as used herein, refers to a line, axis or direction in the plane of the sanitary napkin 10 that is generally aligned with (e.g., approximately parallel to) a vertical plane which bisects a standing wearer into left and right body halves when the sanitary napkin 10 is worn. The terms "transverse" or "lateral" as used herein, are interchangeable, and refer to a line, axis or direction which lies within the plane of the sanitary napkin 10 that is generally perpendicular to the longitudinal direction.

While the topsheet 24, the backsheet 26, and the absorbent core 28 may be assembled in a variety of well known configurations (including so called "tube" products), preferred sanitary napkin configurations are described generally in U.S. Pat. No. 4,950,264, "Thin, Flexible Sanitary Napkin" issued to Osborn III on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987, U.S. Pat. No. 5,009,653 "Thin, Flexible Sanitary Napkin" issued to Osborn III on Apr. 23, 1991, and U.S. Pat. No. 5,308,346 "Elasticized Sanitary Napkin" issued to Sneller, et at. on May 3, 1994; U.S. patent application Ser. No. 07/915,133 "Stretchable Absorbent Article" filed on Jul. 23, 1992 and published on Feb. 4, 1993 as PCT publication WO 93/01785; and U.S. patent application Ser. No. 07/915,284 "Extensible Absorbent Article" filed on Jul. 23, 1992 and published on Feb. 4, 1993 as PCT publication WO 93/01786. The disclosure of each of these patent publications is hereby incorporated herein by reference. FIG. 1 shows a preferred embodiment of the sanitary napkin 10 in which the topsheet 24 and the backsheet 26 have length and width dimensions generally larger than those of the absorbent core 28. The topsheet 24 and the backsheet 26 extend beyond the edges of the absorbent core 28 to thereby form portions of the periphery.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet are non-absorbent and, if properly apertured, have a reduced tendency to allow liquids to pass back through and fewer the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. The disclosure of each of these patent publications is incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so that liquids will transfer through the topsheet faster than if the body surface was not hydrophilic. This will diminish the likelihood that menstrual fluid will flow off the topsheet rather than flowing into and being absorbed by the absorbent core. In a preferred embodiment, the topsheet can be made hydrophilic by treating it with a surfactant such as is described in the above referenced U.S. Pat. Nos. 4,950,254 and 5,009,653 both issued to Osborn, the disclosures of which are incorporated herein by reference.

The absorbent core 28 may be any absorbent means which is capable of absorbing or retaining liquids (e.g., menses and/or urine). As shown in FIG. 1, the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.). The absorbent core 28 can be made from a wide variety of liquid-absorbent materials commonly used in sanitary napkins and other absorbent articles including, but not limited to, comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones or be profiled so as to be thicker in the center). The absorbent core may, for example, also have hydrophilic gradients, superabsorbent gradients, or lower density and lower average basis weight acquisition zones; or it may comprise one or more layers or structures. The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Examples of some types of absorbent structures that could be used as the absorbent core of the present invention are described in U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. A preferred embodiment of the absorbent core 28 of the present invention comprises a layer of superabsorbent material disposed between two air laid tissues as described in U.S. Pat. No. 4,950,264 entitled "Thin, Flexible Sanitary Napkin" issued to Osborn III on Aug. 21, 1990 and U.S. Pat. No. 5,009,653 entitled "Thin, Flexible Sanitary Napkin" issued to Osborn III on Apr. 23, 1991. The disclosure of each of these patent publications is incorporated herein by reference.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin 10 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385. The backsheet is preferably embossed and/or matte finished to provide a more clothlike appearance. Further, the backsheet 26 may permit vapors to escape from the absorbent core 28 (i.e., breathable) while still preventing exudates from passing through the backsheet 26.

The backsheet 26 and the topsheet 24 are positioned adjacent the garment surface and the body surface, respectively, of the absorbent core 28 and are preferably joined thereto and to each other by attachment means such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H.B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, the disclosure of which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The disclosure of each of these patent publications is incorporated herein by reference. Alternatively, the attachment means may comprise heat bonds, pressure bonds, ultrasonic bonds, dynamic mechanical bonds, or any other suitable attachment means or combinations of these attachment means as are known in the art.

Figure 2:
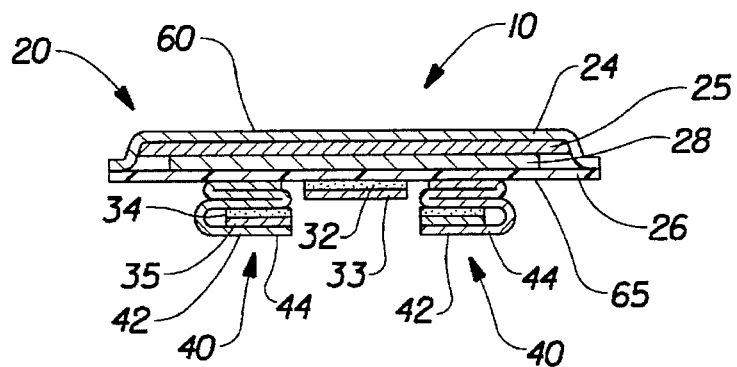
FIG. 2 is a sectional view taken along lines 2—2 of FIG. 1, showing a preferred embodiment of the flap pairs on the sanitary napkin of the present invention.

In the preferred embodiment of the present invention shown in FIGS. 1 and 2, an acquisition component (or components) 25 may either be positioned between the topsheet and the absorbent core, or comprise the bottom surface of a composite topsheet. The acquisition component may serve several functions. These functions include improving wicking of exudates over and into the absorbent core. The improved wicking of exudates is important because it provides a more even distribution of the exudates throughout the absorbent core and allows the sanitary napkin 10 to be made relatively thin. (The wicking referred to herein may encompass the transportation of liquids in one, two, or all directions (i.e., in the x-y plane and/or in the z-direction). The acquisition component may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition component are more fully described in U.S. Pat. Nos. 4,950,264 and 5,009,653 both issued to Osborn, and PCT Patent Publication WO 93/11725 "Absorbent Article Having Fused Layers", issued to Cree, et al. and now pending as U.S. patent application Ser. No. 08/239,084 filed May 6, 1994. The disclosure of each of these references is incorporated herein by reference. In a preferred embodiment, the acquisition component may be joined with the topsheet by any of the conventional means for joining webs together, most preferably by fusion bonds as is more fully described in the above-referenced Cree, et al. patent application.

In use, the sanitary napkin 10 can be held in place by any attachment means 30 well-known for such purposes. Preferably, the sanitary napkin is placed in the user's undergarment or panty and secured thereto by a fastener such as an adhesive. The adhesive provides a means for securing the sanitary napkin in the crotch portion of the undergarment. In the preferred embodiment of the present invention shown in FIGS. 1–4 and the alternative embodiment shown in FIG. 5, there are two different types of attachment means 30. The first type of attachment means is disposed on the central absorbent body 20 and is identified as the pad fastener (or pad adhesive) 32. The second type of attachment means is disposed on the undergarment protection system 40 of the sanitary napkin 10 is identified as the flap fastener (or flap adhesive) 34. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. The pressure-sensitive adhesive is typically covered with a removable release liner in order to keep the adhesive from adhering to a surface other than the crotch portion of the undergarment prior to use. These are identified as the pad release liner 33 and the flap release liner 35 in FIGS. 1–4. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. Suitable release liners are also described in the above-referenced U.S. Pat. No. 4,917,697. The flap release liner 35 may also be releasably joined to an overlying portion of the flap 44 to help maintain the flap in a folded configuration prior to use.

Alternatively, portions or all of the attachment means 30 can comprise a mechanical fastening system. In one embodiment, for example, the pad adhesive 32 and/or the flap adhesive 34 can be replaced with patches of hook material for engaging the wearer's panties. In addition, flap adhesive 34 can be replaced by a hook and loop fastening system. The hook portion of the hook and loop fastening system can be disposed on one flap 44 of each flap pair 42 while the loop portion can be disposed on the other flap 44. In this embodiment the transverse width of a flap pair 42 in its open configuration would be large enough for the flap pair 42 to encircle the crotch portion of a user's undergarment with one flap 44 overlapping the other flap 44 of the flap pair allowing the hook portion of the hook and loop fastening system to engage the loop portion of the hook and loop fastening system to secure the undergarment protection system 40 in place.

The sanitary napkin of the present invention comprises a plurality of flap pairs 42. A preferred embodiment of sanitary napkin 10 which employs three flap pairs A, B, and C is shown in FIGS. 1–5. These flap pairs give a wearer greater flexibility in her choice of positioning for the central absorbent body while still maintaining the added protection advantages of a sanitary napkin with flaps. The preferred embodiment of the present invention shown in FIGS. 1 through 4 comprises three longitudinally related flap pairs 42. Three such pairs have been found to provide a good balance between positioning flexibility and area coverage for protection. The longitudinal length of the flaps in a flap pair can be varied to change this balance between positioning flexibility and protection. Thus, the preferred embodiment shown in FIGS. 1 through 4 should not be taken as limiting the present invention. Rather, a sanitary napkin 10 of the present invention is contemplated to comprise any number of flap pairs 42 as wearer needs would indicate.

The flap pairs 42 can comprise any material or combination of materials known in the art for this purpose. Preferably, each flap pair comprises a thin, flexible, liquid impervious material. A flap pair 42 may thus comprise a woven or nonwoven material, polymeric films such as thermoplastic films of polyethylene or polypropylene, or composite materials such as a film-coated nonwoven material. Preferably, a flap pair comprises a polyethylene film similar to that used for the backsheet 26. A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. The disclosure of each of these patent publications is incorporated herein by reference.

The flap pairs 42 may be joined to the central absorbent body 20 in any suitable manner. As used herein, the term "joined to" encompasses configurations whereby an element is directly secured to another element by affixing the element directly to the other element, and configurations whereby the element is indirectly secured to the other element by affixing the element to an intermediate member(s) which in turn is affixed to the other element. FIGS. 1 and 2 show each flap pair 42 being attached to the backsheet 26 along two parallel, longitudinally extending lines that lie intermediate the centerline 100 and the longitudinal sides 50 of the central absorbent body 20 by any means such as those well known in the art. For example, a flap pair 42 and the backsheet 26 may be secured to each other by a uniform continuous layer of adhesive, a patterned layer of adhesive, or an array of separate lines, spirals, or spots of adhesive or by other means as described above for joining the topsheet 24 and the backsheet 26. Preferably, a flap pair 42 and the backsheet 26 may be secured to each other using thermal bonding. Such bonds can be formed using, for example, a thermal impulse sealer. Such a sealer is available from Vertred Corp., Brooklyn, N.Y. as Model 12H.

Alternatively, the flap pairs 42 can comprise an extension of one or more of the other components of the sanitary napkin. For example, the backsheet 26 or the top sheet 24 and the backsheet 26 could be extended beyond the longitudinal edge 50 of the central absorbent body 20 and folded appropriately to form the flap pairs 42. It is important that flap pairs 42 formed in this manner be impermeable to liquids in order that the flap pairs 42 still protect a user's undergarments from soiling.

Figure 3:
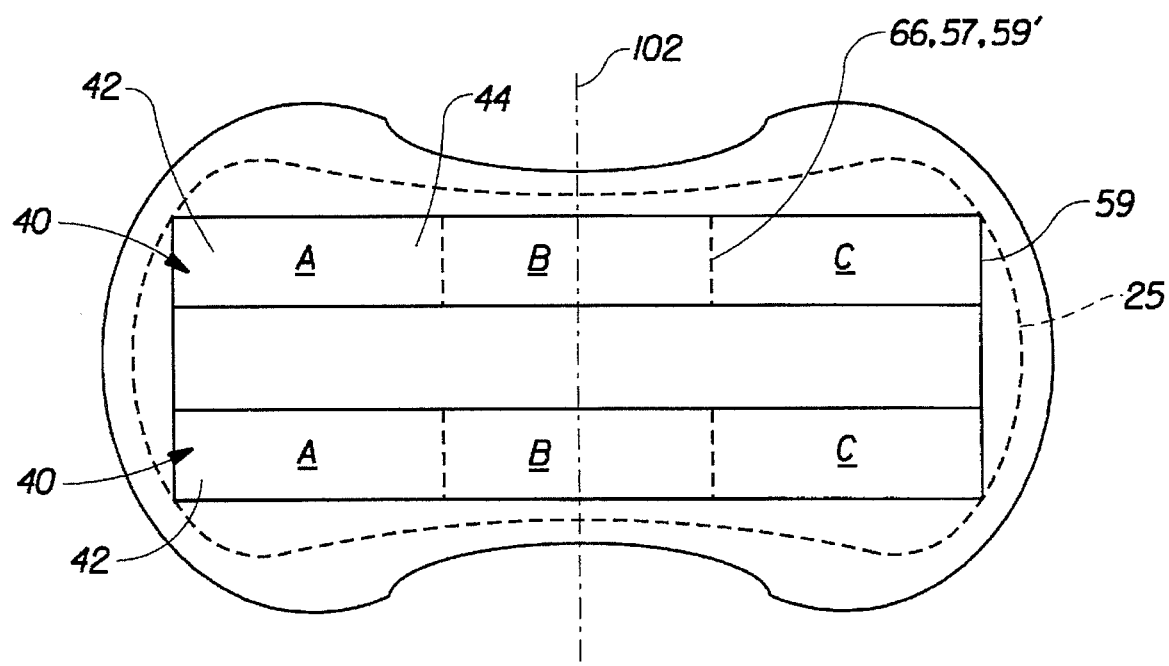
FIG. 3 is a plan view of the garment facing side of a sanitary napkin showing a preferred embodiment of the flap pairs of the present invention in their folded configuration.
Figure 4:
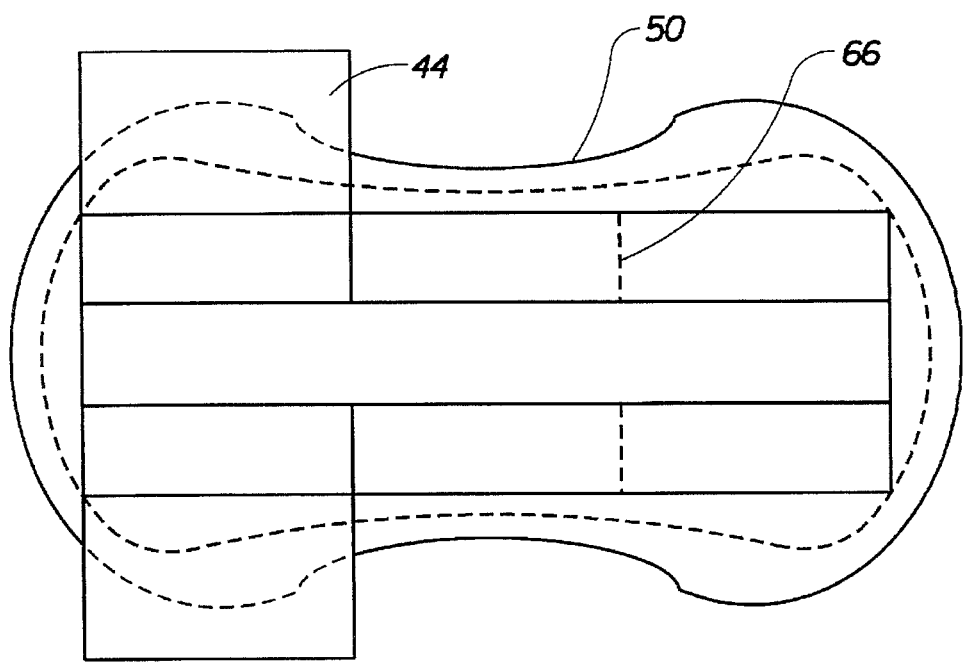
FIG. 4 is a plan view of the garment facing side of a sanitary napkin showing a preferred embodiment of the flap pairs of the present invention with one flap pair shown in an open configuration.

As is most clearly shown in FIGS. 3 and 4, each flap pair, except a pair that overlies the transverse centerline 102, preferably has a central facing transverse edge 57 and an end facing transverse edge 59. The central facing transverse edge 57 is closer to the transverse centerline 102 than is the opposite transverse edge of that flap pair, the end facing transverse edge 59. The central flap pair 42' overlies the transverse centerline 102 and is said to have two end facing transverse edges which are designated 59'. For each set of longitudinally adjacent flap pairs, a central facing transverse edge 57 is joined to the end facing transverse edge 59 along a line of weakness. In the preferred embodiment shown in FIGS. 1 through 4, individual flap pairs 42 are joined longitudinally by the land areas of a perforation pattern 66 (see FIGS. 3 and 4). For example, the central facing transverse edge 57 of the flap pair 42 labeled A in FIG. 3 is joined to the end facing transverse edge 59' of the flap pair 42 labeled B by the land areas of a perforation pattern 66. Alternatively, other means of providing separability between individual flap pairs 42, such as score lines, laser scoring, or the like can be used. One skilled in the art will recognize that this means of joining the individual flap pairs 42 allows relatively simple continuous web processes to be used for fabricating and attaching the flap pairs 42 to the backsheet 26.

The flap pairs 42 can also be joined to the central absorbent body 20 as individual elements. In such an embodiment each flap pair 42 can be joined to the central absorbent body 20 separately. However, the longitudinal relationships among the various flap pairs discussed above may still be maintained. That is, the respective central facing and end facing transverse edges are longitudinally adjacent to each other rather than being joined by a line of weakness. Further, the flaps 44 of a first flap pair in this embodiment can be designed such that they overlap the flaps 44 of a longitudinally adjacent second flap pair 42.

The transverse length of the individual lands in the perforation pattern 66 determines the force required to open and unfold a flap pair 42 into individual flaps 44. Individual flap pairs can thus be separated when the sanitary napkin is used by tearing the flap pairs 42 along selected perforations.

As shown in FIGS. 2 and 3, the flaps 44 of the present invention are in a retracted position prior to use. This retracted position is preferably achieved by providing the flaps 44 with a folded configuration. Each flap 44 of a flap pair 42 can be c-folded, s-folded, z-folded or any other folded configuration as determined by the desired transverse length (or width) of a flap 44. Other suitable configurations in which the flaps may be folded are described in U.S. Pat. No. 5,281,209 issued to Osborn and in PCT Application No. WO 94/00093 published in the name of Lavash, et. al on Jan. 6, 1994 and now pending as U.S. patent application Ser. No. 08/283,925 filed on Aug. 1, 1994.

FIG. 4 shows the flaps 44 of one of the flap pairs 42 in their unfolded or extended configuration. When unfolded, each flap 44 of a flap pair 42 extends transversely beyond one of the longitudinal sides 50 of the central absorbent body 20. The flaps are configured to drape over the edges of the wearer's underwear in the crotch region so that the flaps are disposed between the edges of the wearer's underwear and the wearer's thighs. The flaps serve at least two purposes. First, the flaps help serve to prevent soiling of the wearer's body and underwear by menstrual fluid, preferably by forming a double wall barrier along the edges of the undergarment. Second, the flaps are preferably provided with attachment means on their garment surface so that the flaps can be folded back under the undergarment and attached to the garment facing side of the undergarment, or to the other flap, to hold the sanitary napkin in place. One example of an attachment means is shown as flap adhesive 34 in FIG. 2. In this way, the flaps serve to keep the sanitary napkin properly positioned in the undergarment.

The sanitary napkin 10 of the present invention is used by removing the release liner and thereafter placing the sanitary napkin in an undergarment so that the adhesive contacts the undergarment. The adhesive maintains the sanitary napkin in its position within the undergarment during use. More preferably, to use the sanitary napkin 10 shown in FIGS. 1–4, a wearer would: (1) remove the pad release liner 33 exposing the pad adhesive 32; (2) remove the flap release liner 35 on the flap pair 42 best meeting her comfort and protection needs thereby exposing the flap adhesive 34 disposed on that flap pair 45; (3) unfold the aforementioned flap pair 42; (4) seat the pad adhesive 32 in the crotch area of her undergarment, positioning the central absorbent body 20 in a location that best meets her absorbency needs; (5) fold each opened flap 44 about the edge of her undergarment; and (6) preferably seat the flap adhesive 34 on the garment contacting side of her undergarment.

In an alternative embodiment, flap pairs 42 can comprise a low yield strength film. Such films should have a yield value of no greater than about 252 grams per inch (0.56 pounds/inch) as measured using ASTM method D 882. A suitable tensile tester for such measurements is a Model 4500 tensile machine made by the Instron Corporation of Canton, Mass. The following parameters can be used to set up a tensile tester for such measurements: Crosshead speed—50.8 cm/minute (20 inches/minute); gage length—5.1 cm (2.0 inches); and load cell capacity—2500 g (5.5 pounds). Such materials would not, necessarily need to be in a folded configuration prior to use. That is, rather than unfolding a flap 44, in such an embodiment, a user would stretch the flap in the transverse direction to provide the needed area coverage. The low yield strength requirement for this embodiment of the present invention insures that the force necessary to stretch a flap made using such a material would not be objectionable to a user. Suitable materials are available from Century International Adhesives & Coatings Inc., Columbus, Ohio under the name DSF001 film.

Figure 5:
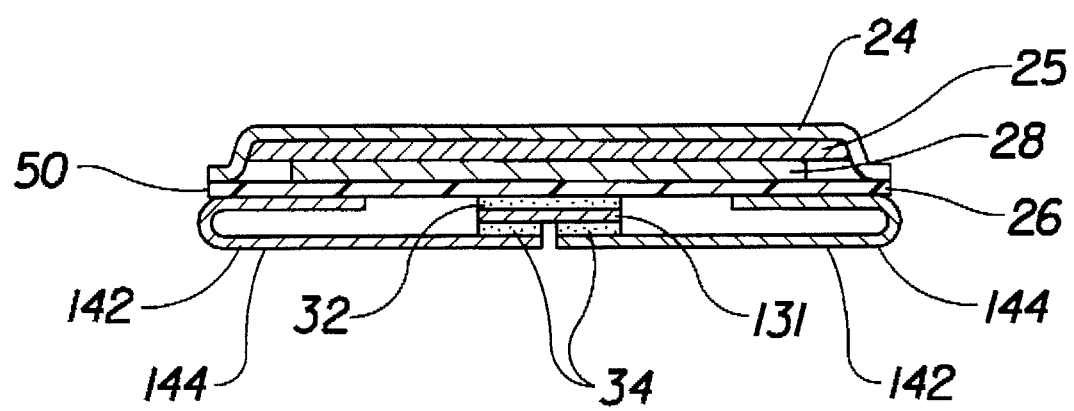
FIG. 5 is a sectional view taken along lines 2—2 of FIG. 1 showing an alternative embodiment of the flap pairs of the present invention.

FIG. 5 shows yet another alternative embodiment of the present invention wherein the folding pattern chosen for the flap pairs 142 provides the additional advantage of reducing the need for a separate flap release liner by using a single release liner 131 for both the pad release liner and the flap release liner. Specifically, in the embodiment shown in FIG. 5, the proximal edge of each flap 144 of a flap pair 142 is joined to the backsheet 26 preferably adjacent the longitudinal side 50 of the central absorbent body 20 using means well known to the art. The flaps are then c-folded and the transverse length of the flaps 144 is chosen such that the distal edge of each flap 144 of a flap pair 142 is adjacent the longitudinal centerline 100 of the central absorbent body 20.

Also as shown in FIG. 5, the pad adhesive 32 is disposed on the central absorbent body adjacent the longitudinal centerline 100. The flap adhesive 34 is disposed on each of the flaps 144 along the distal edge of the flap 144 adjacent the longitudinal centerline 100 when the flap is in a folded configuration. In this embodiment of the present invention, the pad adhesive 32 preferably has roughly twice the transverse width of the flap adhesive 34.

The release liner 131 is positioned intermediate the pad adhesive 32 and the flap adhesive 34 as is also shown in FIG. 5. This release liner 131 differs from those release liners 31 described above in that it has low energy surfaces on both sides. This, combined with the folding pattern and the transverse flap length described above and shown in FIG. 5, allows elimination of that portion of the release liner that has heretofore been necessary to protect that portion of adhesive that is disposed on the flaps of a sanitary napkin. Suitable materials for release liner 131 are manufactured by the Akrosil Corporation of Menasha, Wis.

While particular embodiments of the present invention have been illustrated and described, it would be obvious to those skilled in the art that various other changes and modifications can be made without departing from the spirit and scope of the invention. For example, the multiple flaps of the present invention could also be applied to other absorbent articles such as pantiliners and adult incontinence products that are also inserted into a user's underwear. It is therefore intended to cover in the appended claims all such changes and modifications that are within the scope of this invention.

What is claimed is:

1. A disposable absorbent article for protecting an undergarment form soiling, said absorbent article comprising:
    a central absorbent body having longitudinal and transverse centerline and first and second longitudinal edges, said central absorbent body comprising;
    a liquid pervious topsheet;
    a liquid impervious backsheet joined with said topsheet;
    an absorbent core between said topsheet and said backsheet; and
    an adjustable undergarment protection system joined to said central absorbent body, said adjustable undergarment protection system comprising a plurality of longitudinally adjacent flap pairs arranged so that each of said flap pairs can be separately deployed from a retracted position to an extended position, each of said flap pairs comprising a material, wherein at least one of said plurality of flap pairs is also joined to at least one of said plurality of flap pair longitudinally adjacent thereto along a transverse line of weakness in said material wherein said line of weakness allows controlled tearing of said material.

2. The disposable absorbent article of claim 1 wherein said flap pairs are folded when in said retracted position and comprise at least one folded web.

3. The disposable absorbent article of claim 2 wherein said folded flap pairs comprise first and second folded webs arranged so that said first and second folded webs are on opposite sides of the longitudinal centerline of said central absorbent body.

4. The disposable absorbent article of claim 2 wherein said folded flap pairs are folded in a c-fold.

5. The disposable absorbent article of claim 2 wherein said folded flap pairs are folded in a z-fold.

6. The disposable absorbent article of claim 2 wherein said folded flap pairs are folded in an s-fold.

7. The disposable absorbent article of claim 1 wherein said line of weakness comprises the land areas of a perforation pattern.

8. The disposable absorbent article of claim 1 wherein said line of weakness comprises a score line.

9. The disposable absorbent article of claim 1 wherein said disposable absorbent article further comprises means for attaching said central absorbent body to the undergarment disposed on said central absorbent body.

10. The disposable absorbent article of claim 9 wherein said plurality of flap pairs comprises at least two pairs of folded flaps, wherein each flap of said pair extends transversely beyond said longitudinal edge of said central absorbent body when one of said flap pairs is unfolded, and said absorbent article further comprises means for attaching said flap to the undergarment disposed on said flap.

11. The disposable absorbent article of claim 10 wherein said means for attaching said central absorbent body to said undergarment and said means for attaching said flaps to said undergarment comprise an adhesive.

12. The disposable absorbent article of claim 11 wherein said means for attaching said flaps to said undergarment substantially underlies said means for attaching said central absorbent body to said undergarment; said absorbent article further comprising a releasable liner between said means for attaching said flaps to said undergarment and said means for attaching said central absorbent body to said undergarment which temporarily joins said means for attaching said flaps to said undergarment to said means for attaching said central absorbent body to said undergarment.

13. The disposable absorbent article of claim 10 wherein said means for attaching said central absorbent body to said undergarment comprises an adhesive and said means for attaching said flaps to said undergarment comprises a mechanical fastening system.

14. A unitary sanitary napkin for protecting an undergarment from soiling, said sanitary napkin comprising;
    a liquid pervious topsheet;
    a liquid impervious backsheet joined with said topsheet;
    an absorbent core between said topsheet and said backsheet;
    means for attaching said central absorbent body to said under garment disposed on said central absorbent body; and
    an adjustable undergarment protection system, said adjustable undergarment protection system comprising;
    at least two longitudinally adjacent flap pairs, each of said pairs comprising a material and being joined to said central absorbent body, and each of said flap pairs further comprising;
    two folded flaps, wherein each flap of said pair extends transversely beyond said longitudinal edge of said central absorbent body when one of said paris is unfolded;
    a means for attaching said flap to said undergarment disposed on each of said flaps; and
    each of said flap pairs comprising a material, wherein at least one of said plurality of flap pairs is also joined to at least one of said plurality of flap pair longitudinally adjacent thereto along a transverse line of weakness in said material wherein said line of weakness allows controlled tearing of said material.

15. The sanitary napkin of claim 14 wherein said means for attaching said flaps to said undergarment and said means for attaching said central absorbent body to said undergarment comprise an adhesive.

16. The sanitary napkin of claim 15 wherein said transverse line of weakness comprises the land areas of a perforation pattern.

17. The sanitary napkin of claim 15 wherein said means for attaching said flaps to said undergarment and substantially underlies said means for attaching said central absorbent body to said undergarment; said sanitary napkin further comprising a releasable liner intermediate said means for attaching said flaps to said undergarment and said means for attaching said central absorbent body to said undergarment which temporarily joins said means for attaching said flaps to said undergarment to said means for attaching said central absorbent body to said undergarment.

18. The sanitary napkin of claim 14 wherein said folded flaps are folded in a c-fold.

19. The sanitary napkin of claim 14 wherein said folded flaps are folded in a z-fold.

20. The sanitary napkin of claim 14 wherein said folded flaps are folded in a s-fold.

21. The sanitary napkin of claim 14 wherein said line of weakness comprises a score line.

* * * * *

UNITED STATES PATENT AND TRADEMARK OFFICE
CERTIFICATE OF CORRECTION

PATENT NO. : 5,626,572
DATED : May 6, 1997
INVENTOR(S) : Nicholas Albert Ahr et al.

It is certified that error appears in the above-identified patent and that said Letters Patent is hereby corrected as shown below:

Column 11,
Line 35, "form" should read -- from --.

Column 12,
Line 56, "paris" should read -- pairs --.

Signed and Sealed this

Eighth Day of January, 2002

*Attest:*

JAMES E. ROGAN
*Attesting Officer*  *Director of the United States Patent and Trademark Office*